US00PP19624P2

(12) United States Plant Patent
Lamack

(10) Patent No.: US PP19,624 P2
(45) Date of Patent: Jan. 13, 2009

(54) ***POLYGONATUM* PLANT NAMED 'DOUBLE STUFF'**

(50) Latin Name: *Polygonatum adoratum var. pluriflorum*
Varietal Denomination: Double Stuff

(76) Inventor: William Francis Lamack, 202 Fonthill Dr., Doylestown, PA (US) 18901

( * ) Notice: Subject to any disclaimer, the term of this patent is extended or adjusted under 35 U.S.C. 154(b) by 0 days.

(21) Appl. No.: 11/890,126

(22) Filed: Aug. 2, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Kent L. Bell
(74) *Attorney, Agent, or Firm*—Klarquist Sparkman, LLP

(57) ABSTRACT

A new and distinct *Polygonatum* plant characterized by foliage with a broad white variegated margin, red stems, and excellent vigor.

1 Drawing Sheet

Botanical denomination: *Polygonatum odoratum* var. *pluriflorum.*
Variety designation: 'Double Stuff'.

BACKGROUND OF THE INVENTION

The present invention relates to a new and distinct *Polygonatum* and given the cultivar name of 'Double Stuff' *Polygonatum* is in the family *Convallariaceae.* The new cultivar originated as a naturally occurring branch mutation of *Polygonatum odoratum* var. *pluriflorum* 'Variegatum' (an unpatented plant) in a garden in Pennsylvania. This mutant has proved stable since it was discovered in June of 1997.

SUMMARY OF THE INVENTION

This new *Polygonatum* is distinguished by:

1. Foliage with a broad white variegated margin.
2. Red stems.
3. Excellent vigor.

This new cultivar has been reproduced only by asexual propagation (division and tissue culture). Each of the progeny exhibits identical characteristics to the original plant. Asexual propagation by tissue culture using standard micropropagation techniques with terminal shoots, as done in Canby, Oreg., shows that the foregoing characteristics and distinctions come true to form and are established and transmitted through succeeding asexual propagations. The present invention has not been evaluated under all possible environmental conditions. The phenotype may change with variations in environment without a change in the genotype of the plant.

BRIEF DESCRIPTION OF THE DRAWING

FIG. 1 shows the flowers, foliage, and habit of a two year old *Polygonatum* 'Double Stuff' in April in Canby, Oreg.

DETAILED PLANT DESCRIPTION

The following is a detailed description of the new *Polygonatum* based on observations of two-year-old specimens grown in the ground in full shade in the trial fields in May in Canby, Oreg. Canby is Zone 8 on the USDA Hardiness map.

Temperatures range from a high of 95 degrees F in August to an average of 32 degrees F. in January. Normal rainfall in Canby is 42.8 inches per year. The color descriptions are all based on The Royal Horticultural Society Colour Chart.

Plant:
- *Type.*—herbaceous perennial.
- *Hardiness.*—USDA Zones 4 to 8.
- *Size.*—40 cm wide and 56 cm tall.
- *Form.*—Clumping.
- *Vigor.*—Excellent.
- *Stem.*—5, arching, from short creeping rhizomes, 56 cm tall, 6 mm wide, internodes 2.5 to 7 cm long, glabrous, Greyed Purple 187B on top ⅔ and Yellow Green 146B on bottom ⅓.
- *Roots.*—fibrous network, White 155A.

Leaf:
- *Number.*—12 to 14 per stem.
- *Type.*—Simple.
- *Shape.*—Elliptic to ovate oblong.
- *Arrangement.*—Alternate, sessile.
- *Blade size.*—Grows to 14.5 cm long and 5 cm wide.
- *Margins.*—Entire and slightly undulate.
- *Apex.*—Acuminate and obtuse tipped.
- *Base.*—Obtuse.
- *Venation.*—Parallel.
- *Surface texture.*—Glabrous on both surfaces.
- *Color.*—Topside — Green 137A to 137B in center and at the base, margin White 155D; bottom side — Greyed Green 191A to 191B with the margin White 155D.

Inflorescence:
- *Type.*—Paired at the leaf axils.
- *Number of flowers per scape.*—About 10.
- *Peduncle.*—Grows to 1.5 cm long, 1 mm wide, glandular, Greyed Purple 187B.

Flower Bud:
- *Size.*—10 mm long and 2 mm wide.
- *Shape.*—Ovoid, down facing.
- *Color.*—White 155D.

Flower:
- *Type.*—Perfect.
- *Size.*—15 mm long and 4 mm wide.

*Perianth description.*—15 mm long and 4 mm wide, tubular campanulate, glabrous inside and out; tepal lobes 6 in number, grow to 4 mm long and 1 mm wide, entire, tip acute, White 155D tipped Yellow Green 146D inside and out.

*Pistil description.*—1 in number, 14 mm long and 1 mm wide, Yellow Green 146D overall, ovary 3.5 mm long and 1 mm wide,; style 11 mm long, filiform.

*Stamen description.*—6 in number, 7 mm long, filaments 5.5 mm long, Yellow Green 146D, anthers 1.5 mm long, Yellow White 158A; pollen not seen.

*Bloom period.*—March to April in Canby, Oreg.

*Lastingness of bloom.*—Each flower lasts about a week.

*Fragrance.*—Yes.

Fruit: A berry, none produced.

Seed: None produced.

Pest and Diseases: *Polygonatum* are troubled by snails and slugs. This variety has no known resistances.

I claim:

1. A new and distinct *Polygonatum* plant as herein illustrated and described.

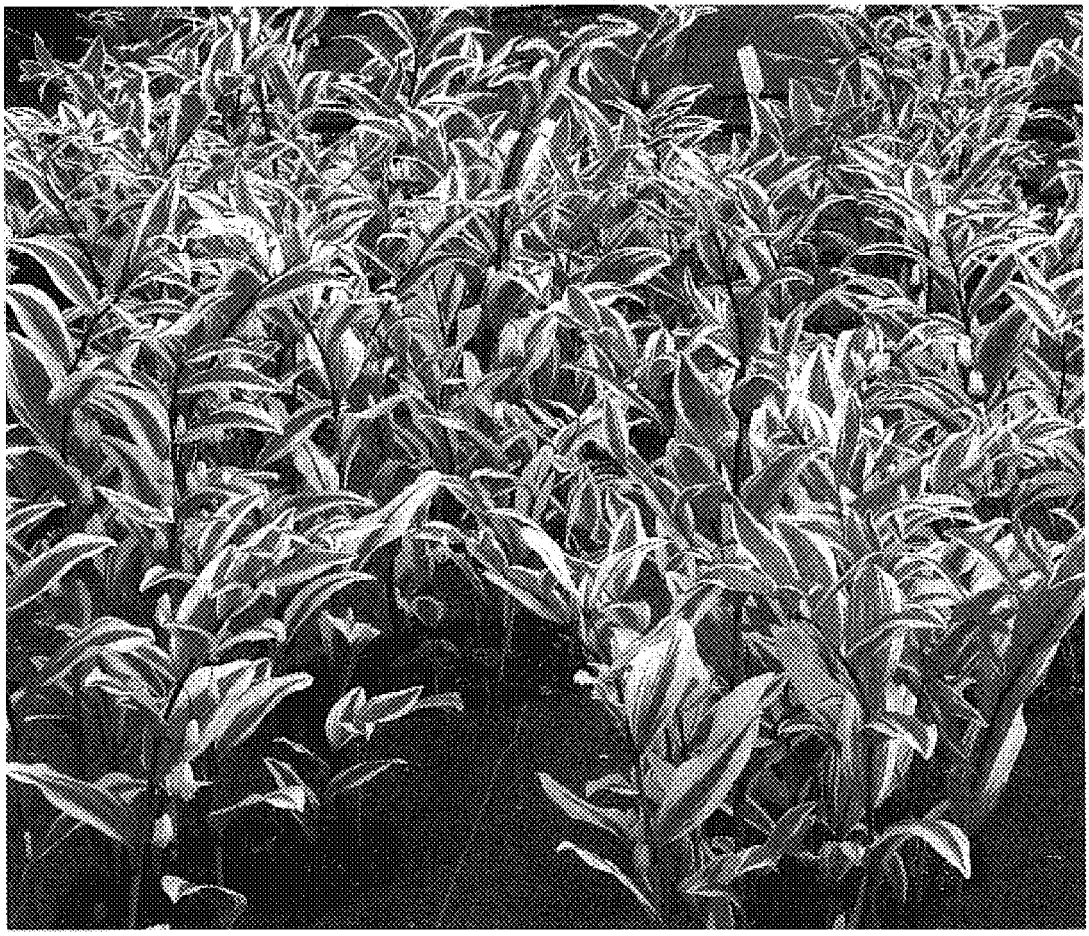

* * * * *